United States Patent [19]

Platz et al.

[11] 4,187,384
[45] Feb. 5, 1980

[54] PREPARATION OF MONO- AND POLY-ETHYLENE GLYCOL DIALKYL ETHERS

[75] Inventors: Rolf Platz, Mannheim; Werner Fuchs, Ludwigshafen; Wolfgang Vodrazka, Freinsheim, all of Fed. Rep. of Germany

[73] Assignee: BASF Aktiengesellschaft, Fed. Rep. of Germany

[21] Appl. No.: 2,336

[22] Filed: Jan. 10, 1979

[30] Foreign Application Priority Data

Jan. 17, 1978 [DE] Fed. Rep. of Germany ....... 2801793

[51] Int. Cl.$^2$ .................. C07C 41/06; C07C 41/10
[52] U.S. Cl. .................................... 568/618; 568/672; 568/697
[58] Field of Search ................ 568/618, 613, 672, 697

[56] References Cited

FOREIGN PATENT DOCUMENTS 2544569  4/1977  Fed. Rep. of Germany ........... 568/618

Primary Examiner—Howard T. Mars
Attorney, Agent, or Firm—Keil & Witherspoon

[57] ABSTRACT

Mono- and poly-ethylene glycol dialkyl ethers I

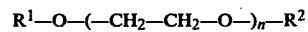

where $R^1$ is $C_1$-$C_4$-alkyl, $R^2$ is $C_3$-$C_5$-alkyl and n is from 1 to 100, are prepared by reacting monoalkyl ethers II

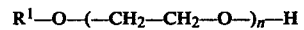

with a $C_3$-$C_5$-olefin III in the presence of an acid ion exchanger at from 1 to 200 bar and from 40° to 150° C., the reaction being started at from 100° to 150° C. and the temperature then being lowered, in at least two approximately equal steps, to from 40° to 80° C., the temperature being dropped in each case to the next-lower level when the conversion per unit time no longer changes significantly.

1 Claim, No Drawings

PREPARATION OF MONO- AND POLY-ETHYLENE GLYCOL DIALKYL ETHERS

The present invention relates to an improved process for the preparation of mono- and poly-ethylene glycol dialkyl ethers of the general formula I $$R^1-O-(-CH_2-CH_2-O-)_n-R^2 \qquad I$$

where $R^1$ is alkyl of 1 to 4 carbon atoms, $R^2$ is alkyl of 3 to 5 carbon atoms and n is from 1 to 100.

German Laid-Open Application DOS No. 2,544,569 discloses the preparation of such compounds by reacting a monoalkyl ether II with an olefin III corresponding to the radical $R^2$, in the presence of an acid ion exchanger at from 2 to 50 bar and from 20° to 150° C.; where propene is the olefin, this reaction corresponds to the following equation:

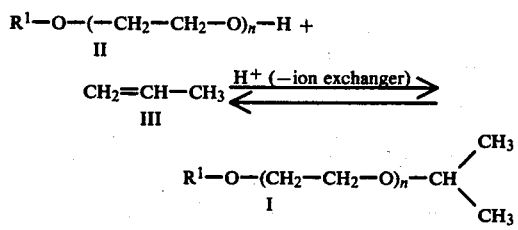

Since the presence of II has a substantial adverse effect on the technological properties of I, but on the other hand unconverted II can virtually not be separated from I, it is necessary to ensure that the conversion of II is virtually complete.

However, there are limits to the extent to which this can be done since, as we have found in connection with the present invention, the reaction is an equilibrium reaction, and with increasing temperature the position of the equilibrium shifts away from the desired products I of the process.

It is an object of the present invention to increase the conversion of the reaction under discussion.

We have found that this object is achieved and that in the process of preparation of mono- and poly-ethylene glycol dialkyl ethers of the general formula I $$R^1-O-(-CH_2-CH_2-O-)_n-R^2 \qquad I$$

where $R^1$ is alkyl of 1 to 4 carbon atoms, $R^2$ is alkyl of 3 to 5 carbon atoms and n is from 1 to 100, by reacting monoalkyl ethers (II)

$$R^1-O-(-CH_2-CH_2-O)_n-H \qquad II$$

with an olefin (III) corresponding to the radical $R^2$, in the presence of an acid ion exchanger, at from 1 to 200 bar and from 40 to 150° C., the conversion can be increased if the reaction is started at from 100° to 150° C. and the temperature is then lowered, in at least two approximately equal steps, to from 40° to 80° C., the temperature being dropped in each case to the next-lower level when the conversion per unit time no longer changes significantly.

Theoretically, the process can be carried out in as many temperature steps as desired, so that the temperature decrease would be progressive. However, for practical reasons it is advisable to lower the temperature stepwise by about 10° to 20° C. at a time.

In the preferred embodiment, wherein the reaction is started at 120° C. and terminated at 80° C., the procedure corresponds to four temperature-lowering steps. The starting temperature is in general the maximum temperature to which the ion exchanger can be exposed continuously without suffering thermal damage.

The statement that the reaction mixture should in each case be kept at a particular temperature level until the conversion per unit time no longer changes significantly means in practice that the initial temperature should be maintained for about 3 hours and that each next step, at a temperature lowered by 10° C., requires about one hour. These times vary somewhat with the amount of catalyst and with the olefin pressure but are virtually independent of the nature of the reactants. The conversion is in each case simple to follow by gas chromatography. The "unit time" is, for purposes of measurement, from about 5 to 60 min, preferably about 10 min.

The monoalkyl ethers II may be obtained in the conventional manner by reacting an alcohol $R^1-OH$ with ethylene oxide in the presence of a catalyst, for example potassium hydroxide. Depending on the ratios of the reactants, and on the reaction conditions, compounds II of different degrees of polymerization n are obtained; as a rule, mixtures of the polymers having the most probable degree of polymerization $n_{max}$ and the degrees of polymerization close thereto are obtained, the distribution being of the conventional Gaussian type. On average, this corresponds to a mean degree of polymerization $\bar{n}$ which in most cases only differs slightly from $n_{max}$. For most technological purposes, compounds I, and hence compounds II, where $\bar{n}$ is from 3 to 60, are preferred. Within the above definition, the nature of the radical $R^1$ has no substantial effect on the properties of I. Hence, for economic and practical reasons, radicals $R^1$ derived from the cheap alcohols methanol, ethanol and isopropanol are preferred.

In the case of the radical $R^2$, again, what matters primarily is that the free —OH group of II should be replaced by a chemically virtually inert ether group as the terminal group. Hence propylene, which is particularly reactive and is industrially readily available, is preferred for the etherification. The stated reaction times apply to propylene and other n-olefins, whilst isobutene, which is even more reactive, requires substantially milder reaction conditions.

The stated limits of the pressure of the olefin are not to be regarded as critical values but as limits within which the reaction may be carried out most economically. Lower pressures retard the reaction excessively whilst higher pressures do not accelerate it to an extent which would justify the greater cost of apparatus and greater energy consumption. In general, it suffices to keep the initial pressure, at which the first process step at the highest temperature is carried out, substantially at the same value for all the temperature steps, but it is also possible to increase the pressure, up to the final stage, by a total of about 50 bar, in order to increase the conversion further.

Suitable strongly acid ion exchangers are in particular crosslinked styrene/divinylbenzene copolymers which carry sulfonic acid groups, such as those commercially available under the trademarks Lewatit ®SPC 118 BG, Amberlite ® 200 and Amberlyst ® 15. The amount of the ion exchanger is preferably from 5 to 20% of the amount of the starting compound II. It is advantageous to use a substantially anhydrous ion exchanger. To remove traces of adhering water, the ion exchanger can, for example, be suspended in benzene, after which the latter is distilled off. On doing so, the water volatilizes as an azeotrope with benzene.

The products I, from which the ion exchanger merely has to be filtered off after completion of the reaction, are valuable aprotic liquids which are particularly suitable for washing gases, because they retain acid constituents such as hydrogen sulfide and carbon dioxide.

In addition, the products may be used as aprotic solvents and extractants, and as hydraulic fluids. The fact that they contain up to 5 percent less of the monoalkyl ethers than do conventionally prepared dialkyl ethers substantially improves their technological properties.

EXAMPLE

A mixture of 1,200 kg of oligoethylene glycol monomethyl ether having a mean degree of oligomerization of 5.5 and 120 kg of the anhydrous strongly acid ion exchanger Lewatit SPC 118 BG was kept in a stirred kettle of 2 m³ capacity under a propylene pressure of 35 bar with vigorous stirring, initially for 3 hours at 120° C., after which the temperature was lowered by 10° C., at a time, at intervals of one hour, until it reached 80° C., the pressure being maintained. According to gas-chromatographic analysis at the end of each reaction stage, the following conversions of monoether were reached:

| Temperature °C. | Duration h | Conversion % |
|---|---|---|
| 120 | 3 | 90.0 |
| 110 | 1 | 93.3 |
| 100 | 1 | 94.8 |
| 90 | 1 | 95.2 |
| 80 | 1 | 96.5 |

For the same total reaction time of 7 hours, the conversion achieved if the temperature was 120° C. throughout was only 93%, whilst if it was 80° C. throughout the conversion achieved was only just 10%.

We claim:

1. A process for the preparation of mono- and polyethylene glycol dialkyl ethers of the general formula I $$R^1-O-(-CH_2-CH_2-O-)_n-R^2 \qquad I$$

where $R^1$ is alkyl of 1 to 4 carbon atoms, $R^2$ is alkyl of 3 to 5 carbon atoms and n is from 1 to 100, by reacting monoalkyl ethers II $$R^1-O-(-CH_2-CH_2-O)_n-H \qquad II$$

with an olefin (III) which corresponds to the radical $R^2$, in the presence of an acid ion exchanger at from 1 to 200 bar and from 40° to 150° C., wherein the reaction is started at from 100° to 150° C. and the temperature is then lowered, in at least two approximately equal steps, to from 40° to 80° C., the temperature being dropped in each case to the next-lower level when the conversion per unit time no longer changes significantly.

* * * * *